US009730959B2

(12) United States Patent
Isaev et al.

(10) Patent No.: US 9,730,959 B2
(45) Date of Patent: Aug. 15, 2017

(54) BIOCOMPOSITE FOR REGENERATION OF INJURED TISSUE AND ORGANS, A KIT FOR MAKING THE BIOCOMPOSITE, A METHOD OF MAKING THE BIOCOMPOSITE AND A METHOD OF TREATING INJURIES

(71) Applicant: "NEXTGEN" COMPANY LIMITED, Moscow (RU)

(72) Inventors: Artur Aleksandrovich Isaev, Moscow (RU); Sergej L'vovich Kiselev, Moscow (RU); Roman Vadimovich Deev, Moscow (RU); Il'ya Yadigerovich Bozo, Kuvshinovo (RU); Elena Sergeevna Filonenko, Timashevsk (RU)

(73) Assignee: "NEXTGEN" COMPANY LIMITED, Moscow (RU)

( * ) Notice: Subject to any disclaimer, the term of this patent is extended or adjusted under 35 U.S.C. 154(b) by 0 days.

(21) Appl. No.: 14/369,008

(22) PCT Filed: Dec. 24, 2012

(86) PCT No.: PCT/RU2012/001103
§ 371 (c)(1),
(2) Date: Jun. 26, 2014

(87) PCT Pub. No.: WO2013/100818
PCT Pub. Date: Jul. 4, 2013

(65) Prior Publication Data
US 2014/0341870 A1    Nov. 20, 2014

(30) Foreign Application Priority Data
Dec. 29, 2011    (RU) ................................ 2011153873

(51) Int. Cl.
*A61K 35/12* (2015.01)
*A61K 47/48* (2006.01)
*A61L 27/12* (2006.01)
*A61L 27/24* (2006.01)
*A61L 27/38* (2006.01)
*A61L 27/46* (2006.01)
*A61L 27/54* (2006.01)
*A61L 27/58* (2006.01)
*A61K 48/00* (2006.01)

(52) U.S. Cl.
CPC ........ *A61K 35/12* (2013.01); *A61K 47/48776* (2013.01); *A61K 48/0041* (2013.01); *A61L 27/12* (2013.01); *A61L 27/24* (2013.01); *A61L 27/3804* (2013.01); *A61L 27/46* (2013.01); *A61L 27/54* (2013.01); *A61L 27/58* (2013.01); *A61L 2300/258* (2013.01); *A61L 2300/64* (2013.01); *A61L 2400/06* (2013.01); *A61L 2430/02* (2013.01)

(58) Field of Classification Search
CPC ............... A61L 27/46; A61L 2300/258; A61L 2300/64; A61L 2400/06; A61L 2430/02; A61L 27/12; A61L 27/24; A61L 27/3804; A61L 27/54; A61L 27/58; C08L 89/06; A61K 35/12; A61K 47/48776; A61K 48/0041
USPC ...................................................... 424/93.21
See application file for complete search history.

(56) References Cited

U.S. PATENT DOCUMENTS

| 5,962,427 A | 10/1999 | Goldstein et al. |
| 6,479,064 B1 | 11/2002 | Atala |
| 2003/0082808 A1* | 5/2003 | Guan ...................... A61L 27/18 435/395 |
| 2004/0266715 A1 | 12/2004 | Wong et al. |
| 2005/0163817 A1 | 7/2005 | Masters et al. |
| 2005/0272153 A1 | 12/2005 | Xuenong et al. |
| 2006/0024377 A1 | 2/2006 | Ying et al. |
| 2007/0212332 A1 | 9/2007 | Baylink et al. |
| 2009/0196901 A1 | 8/2009 | Guilak et al. |

(Continued)

FOREIGN PATENT DOCUMENTS

| RU | 2 170 104 C2 | 7/2001 |
| RU | 2297848 | 4/2007 |
| RU | 2343928 | 1/2009 |

(Continued)

OTHER PUBLICATIONS

International Search Report issued Jun. 14, 2013, in PCT/RU2012/001103, filed Dec. 24, 2012.

(Continued)

*Primary Examiner* — Janet Epps-Smith
(74) *Attorney, Agent, or Firm* — Oblon, McClelland, Maier & Neustadt, L.L.P.

(57) ABSTRACT

Provided is a biocomposite including cells, a genetic construction, and a scaffold and a method for repairing tissue and organs in mammalians with the biocomposite. The interaction of the components of the biocomposite provides a complex effect on reparative regeneration processes. Also provided is a method for administration of gene-cellular therapeutic constructions to a recipient which can be used in medicine and veterinary to provide reparative processes. After administering the biocomposite to a recipient, the scaffold structure releases the nucleic acids which enter into the cells of a recipient bed and cells of the transplanted product. The nucleic acids are expressed, which results in the increased concentration of a target product responsible for reparative processes.

17 Claims, 4 Drawing Sheets

(56) References Cited

U.S. PATENT DOCUMENTS

2011/0229970 A1 9/2011 Ma

FOREIGN PATENT DOCUMENTS

| RU | 2359030 | 6/2009 |
| --- | --- | --- |
| RU | 2 384 618 C2 | 3/2010 |
| RU | 2399667 | 9/2010 |
| RU | 2 407 063 C2 | 12/2010 |
| RU | 2 414 916 C2 | 3/2011 |
| WO | 97/38729 A1 | 10/1997 |
| WO | 97/38729 A8 | 10/1997 |
| WO | WO 02/087411 | 11/2002 |
| WO | 2009/070720 A1 | 6/2009 |

OTHER PUBLICATIONS

Russian Search Report issued Nov. 27, 2012, in Patent Application No. 2011153873/15 (with English Translation of Category of Cited Documents).

Yen-Chen Huang, et al., "Combined Angiogenic and Osteogenic Factor Delivery Enhances Bone Marrow Stromal Cell-Driven Bone Regeneration", Journal of Bone and Mineral Research, vol. 20, No. 5, 2005, pp. 848-857.

Kayabaşi GK, et al., "In vitro chondrogenesis by BMP6 gene therapy", J. Biomed Mater Res A., Oct. 18, 2012, 1 page. (Abstract only).

Kasten P., et al., "Comparison of Platelet-Rich Plasma and VEGF-Transfected Mesenchymal Stem Cells on Vascularization and Bone Formation in a Critical-Size Bone Defect", Cells Tissues Organs, Jul. 10, 2012, 1 page. (Abstract only).

Von Wattenwyl R., et al., "Scaffold-based transplantation of vascular endothelial growth factor-overexpressing stem cells leads to neovascularization in ischemic myocardium but did not show a functional regenerative effect", ASAIO J., vol. 58, No. 3, May-Jun. 2012, pp. 268-274 (Abstract only).

Miao PH, et al., "Impregnation of plasmid DNA into three-dimensional PLGA scaffold enhances DNA expression of mesenchymal stem cells in vitro", Pharmazie, vol. 67, No. 3, Mar. 2012, pp. 229-232 (Abstract only).

Yang X., et al., "Mineralized tissue formation by bone morphogenetic protein-7-transfected pulp stem cells", J Endod, vol. 38, No. 2, Feb. 2012, pp. 170-176 (Abstract only).

Zheng YH, et al., "Basic fibroblast growth factor enhances osteogenic and chondrogenic differentiation of human bone marrow mesenchymal stem cells in coral scaffold constructs", J Tissue Eng Regen Med., vol. 5, No. 7, Jul. 2011, pp. 540-550 (Abstract only).

Wei JI, et al., "Bioactive Electrospun Scaffolds Delivering Growth Factors and Genes for Tissue Engineering Applications", Pharm Res, vol. 28, 2011, pp. 1259-1272.

Wang Qing, et al., "The Osteogenic Study of Tissue Engineering Bone with BMP2 and BMP7 Gene-Modified Rat Adipose-Derived Stem Cell", Journal of Biomedicine and Biotechnology, Article ID 410879, 2012, 7 pages.

Wei Hao, et al., "Enhanced bone formation in large segmental radial defects by combining adipose-derived stem cells expressing bone morphogenetic protein 2 with nHA/RHLC/PLA scaffold", International Orthopaedics (SICOT), vol. 34, 2010, pp. 1341-1349.

Shi-Wu Dong, et al., "Bone Regeneration Using an Acellular Extracellular Matrix and Bone Marrow Mesenchymal Stem Cells Expressing Cbfa1", Biosci. Biotechnol. Biochem., vol. 73, No. 10, 2009, pp. 2226-2233.

Jae-Hyung Jang, et al., "Surface adsorption of DNA to tissue engineering scaffolds for efficient gene delivery", NIH Public Access: Author Manuscript, J. Biomed Mater Res A., vol. 77, No. 1, Apr. 2006, pp. 50-58.

R. Deev, et al., "Angiogenic non-viral gene transfer: from ischemia treatment to bone defects repair", Journal of Tissue Engineering and Regenerative Medicine, vol. 8, (Suppl. 1), 2014, 3 pages (Abstract only).

Bozo I., et al. "Gene Technologies in Maxillofacial Surgery: Development of Gene-Activated Bone Grafts" International Journal of Oral and Maxillofacial Surgery, vol. 42, No. 10, 2013, pp. 1179-1180 (Abstract only).

Bozo I. Y., et al. "Advanced Osteoplastic Material: Gene-activated Bone Graft" Termis-Eu, Jun. 17-20, 2013, Abstract book. p. 403 (Abstract only).

Yaremenko A., et al., "New approach for development of osteoplastic materials: The use of scaffolds with VEGF DNA-plasmid for bone regeneration in a critical size defect model" Materials of 8th Congress of Baltic Association for Maxillofacial and Plastic Surgery, May 10-11, 2013, p. 19 (Abstract only).

Deev R.V., et al., "New approach for development of osteoplastic materials" Bioceramica and Cells for Reinforcement of Bone: Symposium, Oct. 18-20, 2012, p. 32 (Abstract only).

Roman V. Deev, et al., "Current approaches of bone tissue engineering", 3rd Termis World Congress 2012, J. Tissue Eng. Reg. Med, vol. 6 (Suppl. 1), Sep. 5-8, 2012, p. 292 (Abstract only).

International Preliminary Report on Patentability issued Jul. 10, 2014, in International application No. PCT/RU2012/001103.

Written Opinion of the International Searching Authority issued Jun. 14, 2013, in international application No. PCT/RU2012/001103.

Neve A., Cantatore F.P., Corrado A. et al. In vitro and in vivo angiogenic activity of osteoarthritic and osteoporotic osteoblasts is modulated by VEGF and vitamin D3 treatment. Regul. Pept. 2013; 184: 81-4 (Abstract only).

Marini M., Sarchielli E., Toce M. et al. Expression and localization of VEGF receptors in human fetal skeletal tissues. Histol. Histopathol. 2012; 27(12): 1579-87.

Tombran-Tink J., Barnstable C.J. Osteoblasts and osteoclasts express PEDF, VEGF-A isoforms, and VEGF receptors: possible mediators of angiogenesis and matrix remodeling in the bone. Biochem. Biophys. Res. Commun. 2004; 316(2): 573-9 (Abstract only).

Mayr-Wohlfart U., Waltenberger J., Hausser H. et al. Vascular endothelial growth factor stimulates chemotactic migration of primary human osteoblasts. Bone 2002; 30(3): 472-7 (Abstract only).

D' Alimonte I., Nargi E., Mastrangelo F. et al. Vascular endothelial growth factor enhances in vitro proliferation and osteogenic differentiation of human dental pulp stem cells. J. Biol. Regul. Homeost. Agents. 2011; 25(1): 57-69.

Yang Y.Q., Tan Y.Y., Wong R. et al. The role of vascular endothelial growth factor in ossification. Int. J. Oral Sci. 2012; 4(2): 64-8.

Berendsen A.D., Olsen B.R. How vascular endothelial growth factor-A (VEGF) regulates differentiation of mesenchymal stem cells. J. Histochem. Cytochem. 2014; 62(2): 103-8.

Liu Y., Berendsen A.D., Jia S. et al. Intracellular VEGF regulates the balance between osteoblast and adipocyte differentiation. J. Clin. Invest. 2012; 122(9): 3101-13.

First Office Action issued Feb. 2, 2016, in Chinese patent application No. 201280064772.0.

Supplementary Search Report issued Dec. 11, 2014, in European patent application No. 12 86 1904.

Office Action issued Oct. 14, 2015, in European patent application No. 12 861 904.6.

Search Report issued Nov. 27, 2012 in Russian patent application No. 2011153873, as submitted to EPO in European patent application No. 12861904.6.

Deev et al, "Ordinary and Activated Bone Grafts; Applied Classification and the Main Features", 2015, Hindawi Publishing Corp., BioMed Research International, Article ID 365050.

Evans, "Gene Delivery to Bone", 2012, Adv. Drug. Deliv. Rev. 64(12), 1331-1340.

Marshall et al, "Electroporation Mediated Delivery of Naked DNA Plasmid Expressing VEGF to the Porcine Heart Enhances Protein Expression", 2010, Gene Ther, 17(3), 419-423.

Song et al, "Cationic lipid-coated PEI/DNA polyplexes with improved efficiency and reduced cytotoxicity for gene delivery into mesenchymal stem cells", 2012, International Journal of Nanomedicine, , 7, 4637-4648.

(56) References Cited

OTHER PUBLICATIONS

Wang et al, "Polyethylenimine-mediated gene delivery into human bone marrow mesenchymal stem cells from patients", 2011, J. Cell. Mol. Med., 15(9), 1989-1998.

* cited by examiner

BIOCOMPOSITE FOR REGENERATION OF INJURED TISSUE AND ORGANS, A KIT FOR MAKING THE BIOCOMPOSITE, A METHOD OF MAKING THE BIOCOMPOSITE AND A METHOD OF TREATING INJURIES

BACKGROUND OF THE INVENTION

Field of the Invention

An object of the invention pertains to a biocomposite for the use in medicine and veterinary to restore injured tissue and organs in mammalians, to a kit for making the biocomposite, a method of making the biocomposite, a method of treating inquiries, and a method of delivering nucleic acids.

Discussion of the Background

Known methods of tissue and organ restoration are based on engineered tissue constructions that contain either different cell populations or various genetic constructions (nucleic acids). Although both trends—cellular and genetic—are promising, they have moderate and limited efficacy.

A method according to which only a genetic construction is administered with ultrasound is, e.g., described in (Greenleaf W. J., Bolander M. E., Sarkar G. et al. Artificial cavitation nuclei significantly enhance acoustically induced cell transfection. Ultrasound in Medicine and Biology 1998; 24(4): 587-595; Schratzberger P., Krainin J. G., Schratzberger G. et al. Transcutaneous ultrasound augments naked DNA transfection of skeletalmuscle. Molecular Therapy 2002, 6(5): 576-583). However, the efficiency of administration of genetic constructions is low when parameters of ultrasonic radiation safe for a recipient are used. The delivery of the necessary amount of genetic constructions is possible only with the ultrasonic exposure damaging to tissues (see e.g., Duvshani-Eshet M., Machluf M. Therapeutic ultrasound optimization for gene delivery: a key factor achieving nuclear DNA localization. Journal of Controlled Release 2005; 108(2-3): 513-528; Kim H. J., Greenleaf J. F., Kinnick R. R. Ultrasound-mediated transfection of mammalian cells. Human Gene Therapy 1996; 7(11): 1339-1346).

Another method according to which nucleic acids are administered in a complex with liposomes is, e.g., described in (Fraley R., Subramani S., Berg P. et al. Introduction of liposome-encapsulated SV40 DNA into cells. J Biol Chem. 1980; 255(21): 10431-5) and a modified method, i.e., the administration of a combination of a liposome conjugate with genetic constructions using physical factors (e.g., ultrasound) is, e.g., described in (Roos A. K., Eriksson F., Timmons J. A., Skin electroporation: effects on transgene expression, DNA persistence and local tissue environment. PLoS One. 2009; 4(9): e7226). However, a significant proportion of liposomes is destroyed when exposed to lipolytic enzymes in tissue which reduce the efficiency of delivery of active substances such as nucleic acids. The remaining part of nucleic acids is delivered almost concomitantly which does not allow achieving a prolonged effect. Besides, when transported into target cells, a complex "liposome—genetic construction" is not destroyed but rather lyposomes enter the cells which reduces the method safety.

A method according to which nucleic acids are administered via electroporation is, e.g., described in (Roos A. K., Eriksson F., Timmons J. A., Skin electroporation: effects on transgene expression, DNA persistence and local tissue environment. PLoS One. 2009; 4(9): e7226; Schertzer J. D., Lynch G. S. Plasmid-based gene transfer in mouse skeletal muscle by electroporation. Methods Mol Biol. 2008; 433: 115-25). However, this method is based on the application of electric field which pushes genetic constructions (alone or in a complex with other components, e.g., an adjuvant) through a biological membrane. As a result of this method, a significant portion of genetic constructions is damaged. This method does not allow achieving the prolonged effect and, therefore, it is necessity to use the method repeatedly.

A method of locally administering an engineered tissue construction which includes a three-dimensional scaffold and cells adhered to its surface is, e.g., described in (Deev R. V., Tsipkina N. V., Bozo I. Ya., Pinaeva G. P., Tuhiliv R. M., A method of combining cultured osteogenic cells and a three-dimensional matrix-carrier, RU N22008150694, issued Dec. 22, 2008). However, in this set up, the cells require an active blood supply. A critical distance from the hemomicrocirculatory bloodstream, beyond which cells inevitably die, is 200-500 µM (see e.g., Polykandriotis E., Arkudas A., Horch R. et al. Autonomously vascularized cellular constructs in tissue engineering: opening a new perspective for biomedical science. J. Cell Mol. Med. 2007; 11(1): 6-20). Due to this, the size of a tissue-engineered construction, at which the cells of the construction after the transplantation into a recipient remain viable, should be not less 1 cm$^3$.

Defects of a such size do not require additional optimization of the regenerative process, therefore tissue engineering constructions of a significantly larger size can be used (from 1 cm$^3$). However, transplantation of a such large construction may damage a tissue area and may inevitably result in death of a larger proportion of the administered cells (especially the cells located in a central part of the biocomposite) which significantly reduces the efficiency of the method. The effectiveness of a tissue engineering construction in repairing a bone defect (or other applications) mainly depends upon survival of the cells which are comprised in a biocomposite. However, the cells of the tissue engineering construction need oxygenation and, therefore, the bigger tissue engineering construction, the more cells may die after transplantation (especially, the cells located in the central part (closer to the "nucleus") of the tissue engineering construction). Thus, in large tissue engineering constructions (bigger than 1 cm$^3$) many included cells may die and the efficiency of the repair may not be high (e.g., the efficiency may be the same as that of the scaffold without the cells). Therefore, small size tissue engineering constructions are more effective for bone replacement compared to the same scaffold without the cells. This problem of oxygenation is well-known.

In addition, a choice of a size of a tissue engineering construction is determined by the size of a bone defect which has to be repaired; the size of a tissue engineering construction has to match to the size of the bone defect. Thus, small tissue engineering constructions for repair of large defects may not be effectively used. Natural regeneration of small bone defects is quite good and does not require highly effective osteoplastic materials such as tissue engineering constructions. In this case, the regeneration is effective because most of the included cells are alive and perform their function. Thus, tissue engineering constructions are preferably used to repair large bone defects; however, in this case, one have to use tissue engineering constructions of a big size, and the majority of their cells may die and, therefore, the final efficiency becomes lower.

An activated matrix, a method of making the matrix, and local administration of nucleic acids into the matrix of a biocompatible made of various materials to provide reparative processes are, e.g., described in (Goldstein S. A., Methods of in vivo gene transfection for reparative wound regeneration, RU No22170104, issued Jun. 10, 2001). However, these technical approaches are related to a two-component product which includes a scaffold and a genetic construction. In this method, a cellular element which is required for the optimal histotypical restoration of tissue and organs, is absent and, therefore, the efficiency of the product application is moderate.

Thus, various approaches exist for making a biocomposite that provides reparative regeneration of tissue and organs.

One known approach is to combine a scaffold and cells (tissue engineering approach) in a biocomposite. However, when the complex contains a large volume of the biocomposite (greater than 1 cm$^3$), the cells included in the biocomposite after transplantation into a recipient die because of the insufficient blood stream supply. The larger is a biocomposite, the more cells included in the biocomposite and located inside the scaffold die. Only cells located at the periphery survive. This problem of a blood supply of tissue-engineered biocomposites exists and has not been solved up to now.

Another known approach is to combine a scaffold and nucleic acids. However, the "safest" nucleic acids (i.e., nucleic acids carried by a non-viral delivery system, e.g., a plasmid) have a low level of transfection efficiency in vivo, i.e., only from 2 to 5% of the nucleic acids after the implantation of this biocomposite into a recipient transfect the cells. Nucleic acids included in viral delivery systems provide a higher level of transfection (e.g., the efficiency of transfection is up to 40-45%); however, virus-based systems are less "safe", as they are introduced via viral particles (e.g., retrovirus, adenovirus, or lentivirus).

Thus, there is a need in a biological composite which lacks the deficiencies of known methods.

SUMMARY OF INVENTION

An object of the invention pertains to a biocomposite for the use in medicine and veterinary to restore injured tissue and organs in mammalians, to a kit for making the biocomposite, a method of making the biocomposite, a method of treating inquiries, and a method of delivering nucleic acids contained in the biocomposite. An object of the invention has been achieved by the present inventors the first embodiment of which includes a biocomposite comprising a scaffold, at least one nucleic acid and cells which provide reparative regeneration. The biocomposite is suitable for providing reparative processes in injured mammalians.

In another embodiment, the scaffold is a solid organic or inorganic material selected from the group consisting of a metallic material, collagen, chitosan, calcium phosphate, hydroxyapatite, bioceramic, bioglass, alluminate material, purified proteins extracellular matrix products or a combination thereof.

In a different embodiment, the scaffold is at least one liquid selected from the group consisting of a 0.9% NaCL solution, a dextrane solution, a saline solution, a solution of hyaluronic, and a chondroitin-sulphuric acid. Preferably, the scaffold is at least one material selected from the group consisting of a collagen, an alginate, a gelatin gel, a colloidal solution, an ointment, and a cream. In yet, another embodiment, the scaffold comprises at least one material selected from the group consisting of a solid, a liquid, a gel, an ointment and a cream materials. The scaffold can also be nanostructured.

In one embodiment, at least one nucleic acid is in at least one form selected from the group consisting of a DNA-coding gene, a DNA-noncoding gene, a DNA which is included in a vector molecule, a free linear DNAs, a single-stranded RNA, a double-stranded RNA, a RNA with at least one modified ribonucleotide, a 5'-cap-dependent/independent RNA, a 3'-poly(A)-dependent/independent RNA, a microRNA, and a siRNA. Preferably, the nucleic acid encodes at least one gene.

A biocomposite can comprise autogenous and/or allogenous cells. In one embodiment the cells are derivates of one or various cytogenetic lines. Preferably, the biocomposite comprises stem, progenitor or differentiated cells, or a combination of variously differentiated cells.

In one embodiment, the cells are derived from mammalians immediately prior to adding the cells to a biocomposite, or cells which are preliminarily exposed to laboratory technologies of cellular processing.

In a different embodiment, a method of making a biocomposite comprises combining at least one nucleic acid with a scaffold, thereby creating a complex, and adding cells which provide histotypical reparative regeneration to the created complex of the scaffold and the at least one nucleic acid.

In yet another embodiment, a method of making a biocomposite comprises combining at least one nucleic acid with a scaffold, thereby creating a complex, and then adding cells to the created complex, wherein the cells are preliminarily transfected with at least one nucleic acid, which can be the same or different from the at least one nucleic acid combined with the scaffold, and wherein the cells provide histotypical reparative regeneration.

Another embodiment is a method of making a biocomposite comprising preliminary transfecting cells, which provide histotypical reparative regeneration, with at least one nucleic acid and then combining the transfected cells with a scaffold.

In one embodiment, a method for healing injury in a mammalian comprising administering the biocomposite according to the exemplified embodiments to a mammalian in need. Preferably, the biocomposite is administered directly to a damaged tissue area as a part of a surgical operation or manipulation. In a different embodiment, the biocomposite is administered in an intravenous, intra-arterial, intramuscular, intradermic, subcutaneous, intraosteal, endolumbar, subdural, intraarticular, or an orendobulbar injection. In another embodiment, the biocomposite is applied topically.

Provided is also a method of delivery of at least one nucleic acid comprised in the biocomposite, the method comprises administering the biocomposite to a mammalian in need thereof.

In one embodiment, a kit for preparation of a biococomposite comprises a vessel comprising a complex of a scaffold and at least one nucleic acid and a separate vessel for combining the complex with a biological fluid or a culture medium with cells which provide reparative regeneration. In one preferred embodiment, at least one nucleic acid is a DNA which is included in a vector molecule, wherein the vector is a plasmid, a virus, an episome, or a transposon.

The cells can be derived from mammalians immediately prior to adding the cells into the biocomposite, or cells which are preliminarily exposed to laboratory technologies of cellular processing.

In one embodiment, a method of making a biocomposite comprises combining at least one nucleic acid with a scaffold, thereby creating a complex, and then adding cells to the created complex, wherein the cells comprise (i) cells which were preliminarily transfected with at least one nucleic acid, which can be the same or different from the at least one nucleic acid combined with the scaffold, and (ii) cells which were not preliminary transfected, wherein the cells (i) and (ii) provide histotypical reparative regeneration.

In a different embodiment, a biocomposite for providing reparative processes in injured mammalians comprises a scaffold, at least one nucleic acid and cells which provide reparative regeneration.

The details of one or more embodiments of the invention are set forth in the accompanying description below. Although any methods and materials similar or equivalent to those described herein can be used in the practice or testing of the exemplified embodiments, the preferred methods and materials are now described. Other features, objects, and advantages of the exemplified embodiments will be apparent from the description and from the claims. In the specification and the appended claims, the singular forms include plural referents unless the context clearly dictates otherwise. The examples of embodiments are for illustration purposes only.

BRIEF DESCRIPTION OF DRAWINGS

A more complete appreciation of the embodiments and many of the attendant advantages thereof will be readily obtained as the same becomes better understood by reference to the following detailed description when considered in connection with the accompanying drawings, wherein.

DETAILED DESCRIPTION OF THE INVENTION

All publications, patent applications, patents, and other references mentioned herein are incorporated by reference herein in their entirety. Further, the materials, methods, and examples are illustrative only and are not intended to be limiting, unless otherwise specified.

The present inventors have found a new method of histotypical healing injuries in mammalians by administering to a recipient a uniform gene-cellular complex for an optimal (pronounced and prolonged) manifestation of a target action.

The creation and application of new gene-cellular materials allow introduction of a maximum amount of nucleic acids needed for the optimal restoration of tissue and organs of cell elements to a target area, achieving a synergistic and prolonged effect of active components, and also allows prevention of disadvantages found in analogous products.

The new method increases efficacy and efficiency of tissue and organ restoration due to, among others:

optimal delivery of nucleic acids which are protected from damaging factors of a recipient bed in the recipient, as well as prolonged release from a scaffold structure, i.e., a prolonged target effect;

administration of a necessary cell population to a recipient which provides histotypical restoration of tissue and organ integrity; and synergistic effect of nucleic acids and cells included in a uniform medical biocomposite (medical product).

Thus, an object of the exemplified embodiments of this application is a new biocomposite for providing reparative processes in injured mammalians which comprises a scaffold, cells, and at least one nucleic acid.

The interaction of cells and nucleic acids in this biocomposite is akin to symbioses, i.e., the cells provide an increase in the expression level of nucleic acids and act as a delivery-like vehicle, while free nucleic acids (located on the scaffold rather then in the cells of the biocomposite) transfect cells of a recipient (after transplantation of the biocomposite) and expression products of the nucleic acids increase a survival rate of the cells of the biocomposite and/or regulate their morphofunctional activity, depending upon the type of nucleic acids that are used for making a biocomposite (e.g., nucleic acids containing genes of angiogenic, trophic, and any other factors).

In one embodiment, a biocomposite which includes a scaffold, at least one nucleic acid and at least one type of cells providing histotypical reparative regeneration as an agent that provides reparative processes in injured mammalians.

Exemplary nucleic acids are selected from the group consisting of: a DNA-coding gene, DNA-noncoding gene, DNA which is contained in a vector molecule (e.g., plasmids, viruses, episomes, transposones), free linear DNA, single-stranded RNA, double-stranded RNA, RNA with modified ribonucleotides, 5'-cap-dependent/independent RNA, 3'-poly(A)-dependent/independent RNA, microRNA, siRNA, and a combination thereof. The nucleic acids may be included into a composition in several possible variants depending upon a relevant scaffold component. A biocomposite for restoration of tissue and organs contains at least one nucleic acid or their various combinations, wherein at least one nucleic acid may optionally encode at least one gene. In one embodiment, at least one polycassete genetic construction is used.

The selection of a target gene or several target genes contained in the nucleic acid of one type, or the selection of several types of nucleic acids which contain different target genes, to produce a biocomposite depends upon selected materials for tissue and organ restoration which are associated with a biological effect of certain factors encoded by the target gene of the nucleic acids. In one embodiment, it is appropriate to use nucleic acids which encode a vascular endothelial growth factor (VEGF) or stromal cell-derived factor-1 (SDF-1) to restore tissue and organs due to induction of angiogenesis.

A scaffold can be of solid organic or inorganic nature, and may be at least one material selected from the group consisting of: a metallic material, collagen, chitosan, calcium phosphate, hydroxyapatite, bioceramic, bioglass, alluminate material, purified protein, extracellular matrix product, and a combination thereof. In one embodiment, the scaffold is three-dimensional.

A scaffold can be liquid. In one embodiment, the scaffold is at least one solution selected from the group consisting of a 0.9% NaCL solution, a dextrane solution, a saline solution (e.g., a Ringer's, Hank's solution), and an organic acid solution (e.g., components of an amorphous substance of an extracellular matrix (e.g., hyaluronic or chondroitin-sulphuric acid)).

In one embodiment, a scaffold is in at least one form selected from the group consisting of a gel (e.g., collagen, alginate, or gelatin), a colloidal solution, an ointment, and a cream form.

In another embodiment, a scaffold may represent a complex material which contains a solid, liquid, gel, ointment, or cream material and various combinations thereof.

In yet another embodiment, a scaffold may contain at least one nanostructured material. The selection of a cell population is determined by the histogenetic nature of a tissue for which integrity reparation with the derived biocomposite is targeted. To produce a biocomposite, it is appropriate to use such types of cells which are able to differentiate while moving to the cells of damaged tissues or are already differentiated cells corresponding to the cells of the damaged tissue, as well as the cells which are able to provide a process of histotypical reparative regeneration. Such cells include almost any cells which are able to produce necessary growth factors or indirectly optimize a reparative process, e.g., by stimulation and/or angiogenesis.

In one embodiment, a biocomposite contains autogenous and/or allogenous cells. The cells may be derived from one or more cytogenetic lines.

In another embodiment, a biocomposite contains stem, progenitor or differentiated cells, or a combination thereof.

In a different embodiment, a biocomposite contains cells which are derived directly from mammalians, i.e., cells which are used in the biocomposite immediately after they have been obtained from mammalians without applying further laboratory technologies of cellular processing (e.g., without using further culturing, immunophenotyping, and/or induction of differentiation), i.e., so-called "fresh" cells. In one embodiment, the fresh cells are cells that are obtained from a mammalian and are only minimally processed, e.g., centrifuged and/or filtered, and then are immediately administered to the mammalian.

In a different embodiment, a biocomposite contains cells which have been exposed to laboratory technologies of cellular processing (e.g., further culturing, immunophenotyping, induction of differentiation and/or transfection with at least one genetic construction). In one embodiment, the cells may be frozen after being obtained from mammalians.

Provided is also a method of making a biocomposite. Exemplified embodiments of combining components which result in the biocomposite are:

1. Combining at least one nucleic acid with a scaffold and subsequently adding cells, which provide histotypical reparative regeneration, to the derived complex containing the at least one nucleic acid and scaffold.
2. Combining at least one nucleic acid with a scaffold and subsequently adding cells, which have been preliminarily transfected with at least one nucleic acid (the same or different from the nucleic acids combined with the scaffold), to the created complex of the scaffold and the at least one nucleic acid, wherein the cells provide histotypical reparative regeneration to the created complex.
3. Combining at least one nucleic acid with a scaffold, wherein the nucleic acid is preliminarily combined with cells which provide histotypical reparative regeneration, and then the transfected cells are added to the scaffold.
4. Combining, at first, cells with a scaffold and then adding nucleic acids.
5. Combining one cell population with a scaffold, while another cell population is transfected with a genetic construction, and thereafter combining in a biocomposite the transfected cells and the product which includes the cells combined with the scaffold.
6. Combining at least one nucleic acid with a scaffold, and then adding cells to the complex, wherein the cells comprise (i) cells which were preliminarily transfected with at least one nucleic acid, which can be the same or different from the at least one nucleic acid combined with the scaffold, and (ii) cells which were not preliminary transfected, wherein the cells (i) and (ii) provide histotypical reparative regeneration.

The interaction of nucleic acids and a scaffold may be a reversible interaction of a genetic construction with the scaffold components by means of formation of weak (temporary) chemical bonds between the scaffold components and nucleic acids, by means of impregnation of the nucleic acids into the scaffold structure (for example, a liquid, ointment or gel carrier), or by application of the nucleic acids to the surface of a solid scaffold with various adhesive substances. Due to the reversible interaction between the nucleic acids and scaffold, after the biocomposite contacts (interacts) with biological fluids (in particular, after the administration to a recipient), genetic constructions are subsequently released due to certain factors of the recipient bed, and also due to bioresorption of the scaffold (when the scaffold includes bioresorbtive materials). The components of the scaffold which are able to make chemical bonds with nucleic acids may be represented by, for example, hydroxyapatite, fluoroapatite (e.g., Giovannini R., Freitag R. Comparison of different types of ceramic hydroxyapatite for the chromatographic separation of plasmid DNA and a recombinant anti-Rhesus D antiorganism. Bioseparation 2001; 9:359-368), carbonylimidazol (e.g., Sousa A., Tomaz C. T., Sousa F. et al. Successful application of monolithic innovative technology using a carbonyldiimidazole disk to purify supercoiled plasmid DNA suitable for pharmaceutical applications. J Chromatogr A. 2011; 1218(46):8333-43), polyacrylimide (Zhang Y. S., Bai X. F. A simple, rapid and high-resolution banding method in polyacrylamide gels. Yi Chuan. 2008; 30(2):251-4), and/or polymers of methacrylic acid (Smrekar F., Podgornik A., Ciringer M. et al. Preparation of pharmaceutical-grade plasmid DNA using methacrylate monolithic columns. Vaccine 2010; 28(8):2039-45). The scaffold protects an active substance—compartmentalized nucleic acids—from damaging tissue factors of the recipient and allows to prolong the effect due to a temporary chemical bond with the genetic construction. Strength of the chemical bonds between the nucleic acids and scaffold may be different depending upon scaffold materials and a type of the nucleic acids. The strength of the chemical bonds varies from the absence of the bond to almost an irreversible bond.

The interaction of nucleic acids and cells which form a biocomposite is realized through cell transfection with a genetic construction. Nucleic acids may be introduced into the cells both in vitro prior to combining with a scaffold, and as a part of the scaffold when the nucleic acids are first combined with the scaffold, and then cells are added.

The number of nucleic acids for obtaining a biocomposite is defined by the scaffold's capacity, which is the maximum number of nucleic acids which can be located on the surface of the scaffold or within its volume, as well as by the number of nucleic acids which may transfect a cell population to be combined with the scaffold for making a biocomposite. The number of nucleic acids for obtaining a biocomposite depends on the specific situation and can be determined by a skilled person.

Cells which form a biocomposite are adhered to the surface of a solid scaffold due to various mechanisms of cell-matrix and cell-cell interaction, or localized inside a liquid, gel or ointment carrier. The number of the cells which are required for making a biocomposite is defined by the surface area of the scaffold (for a solid scaffold) or by the volume of the scaffold (for a liquid and gel scaffold), and by the lowest required concentration for providing reparative regeneration of a damaged tissue, and also may be determined based on certain conditions.

The synergistic effect of nucleic acids and cells may be different depending on the technology of their combination with the scaffold into a uniform medical product, and depending upon types of genetic constructions and cells. The synergistic effect is implemented at both stages: when a biocomposite (product) is obtained and immediately after its transplantation to a recipient. When preparing a biocomposite, synergy is obtained by cell transfection with nucleic acids (with the entirely pull of nucleic acids in transfection in vitro or by a part of the nucleic acids in transfection after combining with a scaffold), which provides an increase of the number of the introduced nucleic acids, and also allows to optimize properties of a cell population by induction of expression of target genes which are located on the introduced nucleic acids. An effective technology of obtaining the synergistic effect is cell transfection in vitro (a combination of the cells and nucleic acids) and a combination of a scaffold with already transfected cells, a combination of the cells with the complex "scaffold—nucleic acids," cell transfection in vitro and a subsequent combination with the complex "scaffold—nucleic acids." A less effective variant of obtaining the synergistic effect includes a combination of the cells with a scaffold and the subsequent addition of nucleic acids. This technology for the addition of nucleic acids uses reagents and physical factors (e.g., drying) damaging to the cells. When administered to a recipient, genetic constructions, transported by the cells of the recipient's bed and by the cells of the transplanted product, are expressed, and expression products induce and preserve a morphofunctional activity, including activity of the cells introduced into the biocomposite.

In a different embodiment, a method of applying a biocomposite is provided. The biocomposite can be used for effective delivery of nucleic acids to a subject, e.g., mammalians.

The biocomposite may be also used to provide histotypical reparation of injuries in mammalians.

Methods of the biocomposite administration can be different and depend on the form and type of tissue and organ injuries. For example, a biocomposite may be administered immediately to a damaged tissue area as a part of a surgical operation or manipulation. The biocomposite (with a liquid or gel carrier) may be administered to a recipient in the form of injections (e.g., intravenous, intra-arterial, intramuscular, intradermic, subcutaneous, intraosteal, endolumbar, subdural, intraarticular, endobulbar) or may be used in the form of an application (with a liquid, gel, cream, or ointment carrier).

Provided also is a kit for making a biocomposite which includes two components/vessels: one component is for keeping a complex of "scaffold—nucleic acids" in an appropriate vessel, and the other component is for combining the complex of "scaffold—nucleic acids" with a medium or culture fluid and cells and for transportation of the cells.

The first component of the kit is a product having two layers: an internal layer which is sterile inside and outside and is used for keeping a complex of "scaffold—nucleic acids" and for the preservation of its sterility; and an external layer which is sterile only inside, but not outside. The external layer firmly fixes the internal layer and provides sterility of the internal part and protection from a mechanical damage. The external layer can be easily opened without any contact with the internal sterile part.

The second component of the kit, which is for combining the complex of "scaffold—nucleic acids" and cells, represents a sterile vessel made from glass or polymer materials and has a volume required for carrying the scaffold with the nucleic acids and a culture medium or a biological fluid (for example, blood) with the cells. The sterile vessel is also packed with two layers, the internal sterile layer on both sides and the external layer which is sterile inside but not outside.

Thus, the kit for making a biocomposite contains a complex of a scaffold with at least one nucleic acid in one vessel and a second vessel for combining the complex with a biological fluid or a culture medium which contain cells which provide histotypical reparative regeneration.

Having generally described this invention, a further understanding can be obtained by reference to certain specific examples which are provided herein for purposes of illustration only, and are not intended to be limiting unless otherwise specified. It is appropriate to give examples on possible implementation of this invention: making a biocomposite by combination of a scaffold which contains hydroxyapatite and bone collagen, with a population of autogenous blood mononuclear cells and a genetic construction which contains a nucleotide sequence with a VEGF gene (see patent RU 2297848), and its use for reparative regeneration of bone tissue (replacement of the bone defect of 2 cm long in a rabbit shank bone).

EXAMPLES

Example 1

Chemical Binding of a Nucleic Acid and a Scaffold

1. The scaffold preparation. In this example, the combined scaffold was used which included synthetic collagen I type and hydroxyapatite (a ratio was 60%/40%, respectively). Also, the volume of the scaffold was 1 cm$^3$. The scaffold:

a) was washed (incubated in 1 ml of a 0.5 M phosphate solution at 37° C. with constant shaking for 12 hours);

b) equilibrated (processed with 1 ml of 10 mM phosphate at 37° C. with constant shaking, 3 times for 10 min each time); and c) dried (incubated at 37° C. up to the complete drying for 3 hours).

2. The nucleic acid was applied (incubated with a solution containing a DNA plasmid, in 100 µl of 10 mM phosphate at the concentration of 1 µg/µl at 37° C. and with constant shaking for 12 hours) considering the estimated scaffold capacity for nucleic acids, which in this example was 202.765 ng of the nucleic acids per 1 mg of the scaffold.

103. Processing the created complex "scaffold—genetic construction." The complex a) was washed (processed with 1 ml of a 5 mM phosphate solution for 3 times); and b) dried (incubated at 37° C. up to the complete drying for 3 hours).

4. The complex of "scaffold—nucleic acids" was combined with a population of autogenic blood mononuclear cells, wherein the cells were obtained immediately prior to a surgery (during the performance of the surgery). 1 cm$^3$ by volume of the complex of "scaffold—nucleic acids" was transferred into a vessel containing 5 ml of patient's blood withdrawn by a syringe from the damaged tissue area when a surgery was conducted. The exposure lasted for several minutes, i.e., for the time period sufficient to fill in all of the scaffold pores carrying the nucleic acids by blood which contains autogenous mononuclear cells providing histotypical reparative regeneration of the bone tissue.

Example 2

Transplantation of the Complex Created in Example 1

In the transplantation of the medical product (biocomposite), a bone defect of 2 cm long in a rabbit shank bone was used as a model for this experiment. First, Kirschner's wires were placed to fix diastasis and the limb's axis after which the biocomposite was administered to the bone defect.

FIGS. 1-4 illustrate data which confirm the efficacy and efficiency of administration of the chemically compartmentalized genetic material and cells to provide reparative osteogenesis.

To confirm the chemical binding of the nucleic acid and scaffold from the osteoplastic material after washing and drying the created product, dissociation was performed, i.e., destruction of the bond and release of the nucleic acid into solution. For that, the product was processed with 50 µl of a 0.5 M phosphate solution at 37° C. and constant shaking for 10 minutes, and then spectrophotometry of the solution with the eluted nucleic acid was performed (spectrophotometer Nanodrop-1000). As a result, the concentration of the nucleic acids in the solution was measured as 202.765 ng per each mg of the scaffold (various scaffolds have different capacities).

Figure 1:
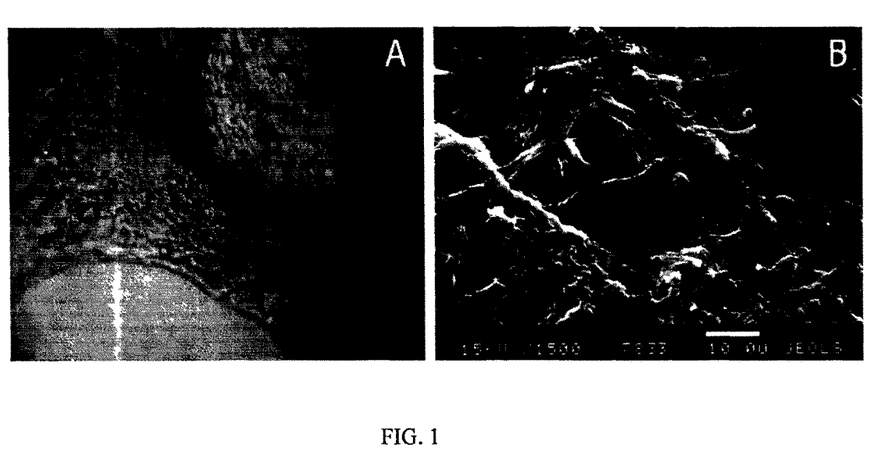
FIG. 1 shows a biocomposite which includes cells and nucleic acids combined with a scaffold from an osteoplastic material. A—light microscopy, B—scanning electron microscopy.
Figure 2:
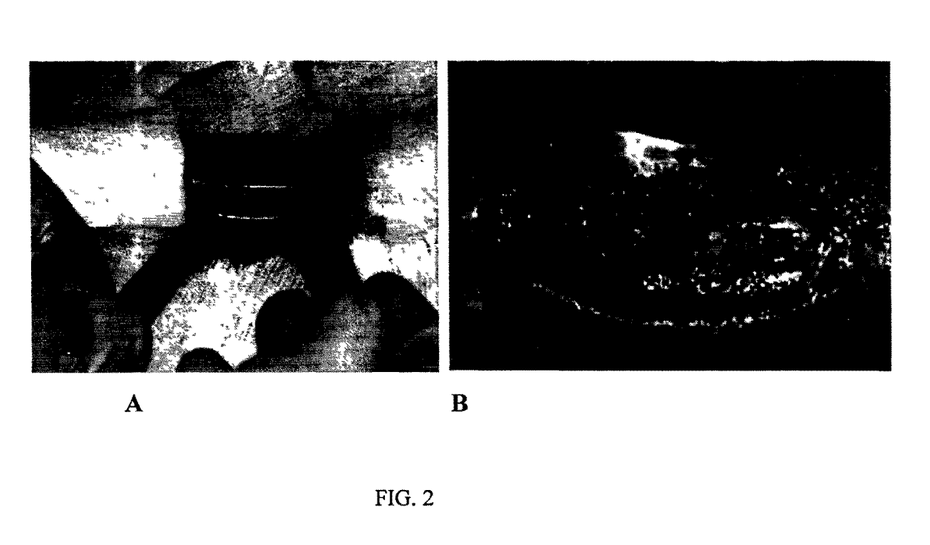
FIG. 2 shows a stage of transplantation of a medical product (biocomposite) in the experiment. A indicates a bond defect prior to administration of the biocomposite, wherein Kirschner's wires were placed to fix diastasis and limb axis. B indicates a biocomposite which is administered to the bone defect.
Figure 3:
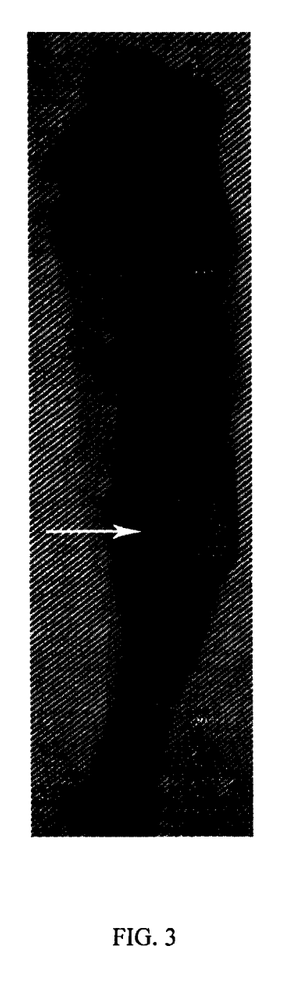
FIG. 3 shows a rabbit shank bone. The bone regenerate is defined in the central part (marked by a white arrow) which was produced with the biocomposite.
Figure 4:
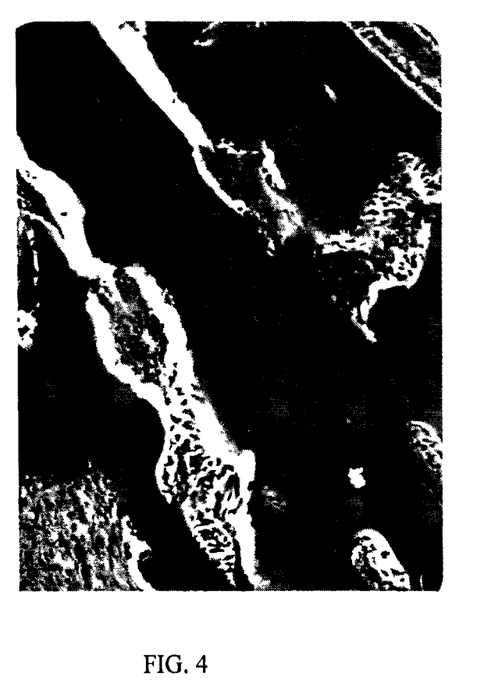
FIG. 4 shown bone regenerate which was formed after administration of a chemically compartmentalized genetic material and cells. A histological picture is shown. Staining: hematoxylin and eosin. Light microscopy: Magnification ×100.

To confirm feasibility of the combination of a population of autogenous blood mononuclear cells with the product-biocomposite, light microscopy of the product was performed and the cells which adhered to the scaffold surface were identified. The methods of light, scan and transmission electronic microscopy showed that the cells which adhered to the matrix were spread and covered almost the entire empty surface of the scaffold (FIG. 1).

This example shows feasibility of the combination of nucleic acids, cells and scaffold, possibility of administration of the created medical product to a recipient, and also demonstrates more rapid and effective restoration of the bone integrity in a rabbit shank bone compared to the closest analogues, wherein the result of this experiment was obtained one month earlier when the new biocomposite was used.

Example 3

The complexes were prepared which include the following scaffold materials (each material in a different scaffold) and nucleic acids in the amounts indicated below:
   calcium phosphate was combined with 72.5 ng of nucleic acids per 1 mg of this scaffold;
   hydroxyapatite was combined with 347.8 ng of nucleic acids per 1 mg of this scaffold;
   extracellular matrix producyss (allogenic demineralized bone matrix) was combined with 108.4 ng of nucleic acids was per 1 mg of this scaffold;
   extracellular matrix producyss (xenogenic deproteinized bone matrix) was combined with 285.7 ng of nucleic acids per 1 mg of this scaffold; and
   a composition of calcium phosphate and hydroxyapatite was combined with 520.1 ng of nucleic acids per 1 mg of this scaffold.

Each of these examples were performed with the aid of the technology (protocol) described in Example 1. Cells were added to the complex of the scaffold and nucleic acids at the second step.

Different types of cells (which were obtained by different technologies) for specific scaffolds were: a culture of multipotent mesenchymal stromal cells, culture of fibroblasts, culture of periostal osteogenic cells; or fresh blood with cells, or stromal vascular cells fraction, obtained with the special apparatus (e.g., Cytori).

These variants of the biocomposite were made according to the protocol of Example 1, had the bone defects repair properties and were tested on the model described in Example 2.

Example 4

A number of the created biocomposites were tested on the model with cranial bone defects.

Cranial defects (diameter 10 mm) of parietal bones were chosen as the model of critical size bone defects. The bilateral identical defects were made to every animal (rabbits). The biocomposites (a complex of a scaffold and a plasmid carrying a vegf-gene), to which fresh autologous blood was added immediately before implantation into the bone defects, were implanted into the defects of right parietal bones (experimental group) while the scaffold without nucleic acids and cells (fresh blood) both (control 1), or the scaffold with the blood cells only (control 2), or the scaffold with the nucleic acids only (control 3) were used for the left side of cranium. Results were evaluated in 15, 30, 45, 60, 90 days.

It was shown that for the biocomposites of the example groups, the transfection of the recipient bed cells by the plasmid carrying cDNA of a vegf-gene was higher which resulted in more pronounced angiogenesis and reparative osteogenesis at all tested time points compared to that of all of the control groups.

The exemplified embodiments are applicable in medical practice, especially for stimulation of reparative processes in tissue, as well as in veterinary for treatment of mammalians.

RU patent application No. 2011153873, filed Dec. 29, 2011, is incorporated herein by reference.

Numerous modification and variations on this invention are possible in light of the above teachings. It is therefore to be understood that within the scope of the appended claims, this invention may be practiced otherwise than as specifically described herein.

The invention claimed is:

1. A biocomposite suitable for providing reparative processes in injured mammalians consisting of:
   a three-dimensional solid material matrix as a scaffold consisting of at least one calcium phosphate,
   at least one nucleic acid encoding vascular endothelial growth factor (VEGF), stromal cell-derived factor (SDF), or VEGF and SDF, and
   cells which provide reparative regeneration, wherein the cells are selected from the group consisting of multipotent mesenchymal stromal cells, fibroblasts, periostal osteogenic cells, fresh blood with cells, and stromal vascular cells fraction.

2. The biocomposite according to claim 1, wherein the at least one nucleic acid is a DNA which is included in a vector molecule, wherein the vector is a plasmid, a virus, an episome, or a transposone.

3. The biocomposite according to claim 1, which comprises autogenous and/or allogenous cells.

4. The biocomposite according to claim 1, wherein the cells are derived from mammalians immediately prior to adding the cells to the biocomposite, or cells which were preliminarily exposed to laboratory technologies of cellular processing.

5. A method of making a biocomposite, the method comprising:
    combining at least one nucleic acid encoding vascular endothelial growth factor (VEGF), stromal cell-derived factor (SDF), or VEGF and SDF with a three-dimensional solid material matrix as a scaffold, thereby creating a complex, and
    adding cells which provide histotypical reparative regeneration to the created complex of the scaffold and the at least one nucleic acid,
    wherein the scaffold consists of at least one calcium phosphate, and
    wherein the cells are selected from the group consisting of multipotent mesenchymal stromal cells, fibroblasts, periostal osteogenic cells, fresh blood with cells, and stromal vascular cells fraction.

6. The method according to claim 5, further comprising deriving the cells from mammalians immediately prior to the adding the cells or preliminarily exposing the cells to laboratory technologies of cellular processing.

7. A method of making a biocomposite, the method comprising:
    combining at least one nucleic acid encoding vascular endothelial growth factor (VEGF), stromal cell-derived factor (SDF), or VEGF and SDF with a three-dimensional solid material matrix as a scaffold, thereby creating a complex, and
    adding cells to the created complex, wherein the cells comprise
        (i) cells which were preliminarily transfected with at least one nucleic acid, which can be the same or different from the at least one nucleic acid combined with the scaffold, and
        (ii) cells which were not preliminary transfected,
    wherein the cells (i) and (ii) provide histotypical reparative regeneration,
    wherein the scaffold consists of at least one calcium phosphate, and
    wherein the cells are selected from the group consisting of multipotent mesenchymal stromal cells, fibroblasts, periostal osteogenic cells, fresh blood with cells, and stromal vascular cells fraction.

8. A method of making a biocomposite, the method comprising:
    combining at least one nucleic acid encoding vascular endothelial growth factor (VEGF), stromal cell-derived factor (SDF), or VEGF and SDF with a three-dimensional solid material matrix as a scaffold, thereby creating a complex,
    preliminarily transfecting cells with at least one nucleic acid, which can be the same or different from the at least one nucleic acid combined with the scaffold, wherein the cells provide histotypical reparative regeneration, and
    adding the transfected cells to the created complex,
    wherein the scaffold consists of at least one calcium phosphate, and
    wherein the cells are selected from the group consisting of multipotent mesenchymal stromal cells, fibroblasts, periostal osteogenic cells, fresh blood with cells, and stromal vascular cells fraction.

9. A method of making the biocomposite, the method comprising:
    preliminary transfecting cells, which provide histotypical reparative regeneration, with at least one nucleic acid encoding vascular endothelial growth factor (VEGF), stromal cell-derived factor (SDF), or VEGF and SDF, and
    combining the transfected cells with a three-dimensional solid material matrix as a scaffold,
    wherein the scaffold consists of at least one calcium phosphate, and
    wherein the cells are selected from the group consisting of multipotent mesenchymal stromal cells, fibroblasts, periostal osteogenic cells, fresh blood with cells, and stromal vascular cells fraction.

10. A method for healing injury comprising administering the biocomposite according to claim 1 to a mammalian in need thereof.

11. The method according to claim 7, further comprising administering the biocomposite directly to a damaged tissue area as a part of a surgical operation or manipulation.

12. The method according to claim 7, further comprising administering the biocomposite in an intravenous, intra-arterial, intramuscular, intradermic, subcutaneous, intraosteal, endolumbar, subdural, intraarticular, or an orendobulbar injection.

13. The method according to claim 7, further comprising topically applying the biocomposite.

14. A method of delivery of at least one nucleic acid comprised in the biocomposite according claim 1 to a mammalian in need thereof, the method comprises applying the biocomposite to the mammalian.

15. A kit for preparation of the biococomposite according to claim 1, comprising:
    a first vessel comprising a complex of a three-dimensional solid material matrix as a scaffold and at least one nucleic acid encoding vascular endothelial growth factor (VEGF), stromal cell-derived factor (SDF), or VEGF and SDF, wherein the scaffold consists of at least one calcium phosphate, and
    a second separate vessel for combining the complex with a biological fluid or cultural medium with cells which provide reparative regeneration, wherein the cells are selected from the group consisting of multipotent mesenchymal stromal cells, fibroblasts, periostal osteogenic cells, fresh blood with cells, and stromal vascular cells fraction.

16. A biocomposite suitable for providing reparative processes in injured mammalians comprising:
    a three-dimensional solid material matrix as a scaffold,
    at least one nucleic acid encoding vascular endothelial growth factor (VEGF), stromal cell-derived factor (SDF), or VEGF and SDF, and
    cells which provide reparative regeneration,
    wherein the scaffold consists of at least one of calcium phosphate, and wherein the cells are selected from the group consisting of multipotent mesenchymal stromal cells, a stromal vascular cells fraction, and cells of fresh blood.

17. The biocomposite of claim 1, wherein the scaffold and the at least one nucleic acid create a complex.

* * * * *